(12) United States Patent
Watson

(10) Patent No.: US 11,278,519 B2
(45) Date of Patent: Mar. 22, 2022

(54) COMPOSITIONS AND METHODS FOR THE TREATMENT AND PREVENTION OF COGNITIVE DECLINE AND PRESERVATION OF NEURONAL FUNCTION

(71) Applicant: Senescence Life Sciences Pte. Ltd., Singapore (SG)

(72) Inventor: Shawn Nathan Watson, Singapore (SG)

(73) Assignee: Senescence Life Sciences Pte. Ltd., Singapore (SG)

( * ) Notice: Subject to any disclaimer, the term of this patent is extended or adjusted under 35 U.S.C. 154(b) by 39 days.

(21) Appl. No.: 16/632,256

(22) PCT Filed: Jul. 18, 2018

(86) PCT No.: PCT/IB2018/055348
§ 371 (c)(1),
(2) Date: Jan. 17, 2020

(87) PCT Pub. No.: WO2019/016731
PCT Pub. Date: Jan. 24, 2019

(65) Prior Publication Data
US 2020/0170995 A1 Jun. 4, 2020

Related U.S. Application Data

(60) Provisional application No. 62/533,926, filed on Jul. 18, 2017.

(51) Int. Cl.
| | | |
|---|---|---|
| *A61K 31/355* | (2006.01) |
| *A61K 9/48* | (2006.01) |
| *A61K 31/198* | (2006.01) |
| *A61K 31/385* | (2006.01) |
| *A61K 31/704* | (2006.01) |
| *A61K 36/23* | (2006.01) |
| *A61K 36/258* | (2006.01) |
| *A61K 47/02* | (2006.01) |
| *A61K 47/12* | (2006.01) |
| *A61K 47/38* | (2006.01) |

(52) U.S. Cl.
CPC .......... *A61K 31/355* (2013.01); *A61K 9/4808* (2013.01); *A61K 31/198* (2013.01); *A61K 31/385* (2013.01); *A61K 31/704* (2013.01); *A61K 36/23* (2013.01); *A61K 36/258* (2013.01); *A61K 47/02* (2013.01); *A61K 47/12* (2013.01); *A61K 47/38* (2013.01)

(58) Field of Classification Search
CPC .. A61K 31/355; A61K 9/4808; A61K 31/198; A61K 31/385; A61K 31/704; A61K 36/23; A61K 36/258; A61K 47/02; A61K 47/12; A61K 47/38
See application file for complete search history.

(56) References Cited

U.S. PATENT DOCUMENTS

| 6,733,797 B1 | 5/2004 | Summers |
| 2013/0034530 A1* | 2/2013 | Fantz ..................... A23L 33/15 424/94.2 |
| 2014/0141082 A1 | 5/2014 | Gao |
| 2016/0235822 A1 | 8/2016 | Holstein et al. |

FOREIGN PATENT DOCUMENTS

WO    WO-2012/143860 A1    10/2012

OTHER PUBLICATIONS

Akiba et al., "Cellular function of calcium-independent phospholipase A2," Biol Pharm Bull. 27(8): 1174-8 (2004).
Anderson P., "Assessment and development of executive function (EF) during childhood," Child Neuropsychol. 8(2): 71-82 (2002).
Angelova et al., "Oxidative modulation of the transient potassium current IA by intracellular arachidonic acid in rat CA1 pyramidal neurons," Eur J Neurosci. 23(9): 2375-84 (2006).
Aoyama et al., "Regulation of neuronal glutathione synthesis," J Pharmacol Sci. 108(3): 227-38 (2008).
Atkinson et al., "Tocopherols and tocotrienols in membranes: a critical review," Free Radic Biol Med. 44(5): 739-64 (2008).
Bak et al., "Detoxifying effect of fermented black ginseng on H2O2-induced oxidative stress in HepG2 cells," Int J Mol Med. 34(6): 1516-22 (2014).
Bigler et al., "Rey-auditory verbal learning and Rey-Osterrieth complex figure design performance in Alzheimer's disease and closed head injury," J Clin Psychol. 45(2): 277-80 (1989).
Boake C., "Edouard Claparede and the auditory verbal learning test," J Clin Exp Neuropsychol. 22(2): 286-92 (2000).
Boland et al., "Polyunsaturated fatty acid modulation of voltage-gated ion channels," Cell Biochem Biophys. 52(2): 59-84 (2008).
Butterfield et al., "Involvements of the lipid peroxidation product, HNE, in the pathogenesis and progression of Alzheimer's disease." Biochim Biophys Acta. 1801(8): 924-9 (2010).
Butterfield et al., "Lipid peroxidation and protein oxidation in Alzheimer's disease brain: potential causes and consequences involving amyloid beta-peptide-associated free radical oxidative stress," Free Radic Biol Med. 32(11): 1050-60 (2002).
Choe et al., "Lipid peroxidation contributes to age-related membrane rigidity," Free Radic Biol Med. 18(6): 977-84 (1995).

(Continued)

*Primary Examiner* — Robert A Wax
*Assistant Examiner* — Olga V. Tcherkasskaya
(74) *Attorney, Agent, or Firm* — Clark & Elbing LLP

(57) ABSTRACT

Described herein are compositions and methods for the treatment and prevention of cognitive decline in subjects. Generally, among other potential components, the compositions comprise *Centella asiatica* or an extract thereof; α-tocopherol or a derivative thereof; *Ginseng* or an extract thereof; a selenium compound, and α-lipoic acid. Also provided are methods of making such compositions.

11 Claims, 12 Drawing Sheets

(56) References Cited

OTHER PUBLICATIONS

Choi et al., "Antioxidantive, phospholipase A2 inhibiting, and anticancer effect of polyphenol rich fractions from Panax ginseng," J Korean Soc Agric Chem Biotechnol. 46(3): 251-256 (2003).
Choi et al., "Brain synaptosomal aging: Free radicals and membrane fluidity," The University of Texas Health Science Center. 18(2): 133-139 (1995).
Choi, D.W., "Calcium-mediated neurotoxicity: relationship to specific channel types and role in ischemic damage," Trends Neurosci. 11(10): 465-9 (1988).
Cini et al., "Studies on lipid peroxidation and protein oxidation in the aging brain," Neurobiology of Aging. 16(1): 53-57 (1995).
Colbert et al., "Arachidonic acid reciprocally alters the availability of transient and sustained dendritic K(+) channels in hippocampal CA1 pyramidal neurons," J Neurosci. 19(19): 8163-8171 (1999).
Danthi et al., "Modulation of native T-type calcium channels by omega-3 fatty acids," Biochem Biophys Res Commun. 327(2): 485-93 (2005).
Defillipo et al., "Inhibition of cPLA2 and sPLA2 activities in primary cultures of rat cortical neurons by Centella asiatica water extract," Nat Prod Commun. 7(7): 841-3 (2012).
Delaney et al., "VA epilepsy cooperative study #264 research group, test-retest comparability and control subject data for the Rey-auditory verbal learning test and Rey-Osterrieth/Taylor complex figures," Arch Clin Neuropsychol. 7(6): 523-8 (1992).
Denson et al., "Effects of fatty acids on BK channels in GH(3) cells," Am J Physiol Cell Physiol. 279: C1211-1219 (2000).
Dobbs et al., "Adult age differences in working memory," Psychol Aging. 4(4): 500-3 (1989).
Dodrill CB., "A neuropsychological battery for epilepsy," Epilepsia. 19(6): 611-23 (1978).
Ekman et al., "Unmasking the face: A guide to recognizing emotions from facial cues," (212 pages) (1975).
Erin et al., "Formation of alpha-tocopherol complexes with fatty acids. A hypothetical mechanism of stabilization of biomembranes by vitamin E," Biochim Biophys Acta. 774(1): 96-102 (1984).
Erin et al., "Formation of alpha-tocopherol complexes with fatty acids. Nature of complexes," Biochimica et biophysica acta. 815: 209-214 (1985).
Espinoza et al., "Glutathione peroxidase enzyme activity in aging," J Gerontol A Biol Sci Med Sci. 63(5): 505-9 (2008).
Etherton et al., "Sensitivity and specificity of reliable digit span in malingered pain-related disability," Assessment. 12(2): 130-6 (2005).
Everatt et al., "The incidence of Stroop interference in dyslexia," Dyslexia. 3(4): 222-228 (1997).
Gamper et al., "Oxidative modification of M-type K(+) channels as a mechanism of cytoprotective neuronal silencing," EMBO J. 25(20): 4996-5004 (2006).
Gray et al., "Lipofuscin and aging: a matter of toxic waste," Sci Aging Knowledge Environ. 2005(5): re1 (2005).
Greilberger et al., "Malondialdehyde, carbonyl proteins and albumin-disulphide as useful oxidative markers in mild cognitive impairment and Alzheimer's disease," Free Radic Res. 42(7): 633-8 (2008).
Hermann et al., "Phospholipase A2—nexus of aging, oxidative stress, neuronal excitability, and functional decline of the aging nervous system? Insights from a snail model system of neuronal aging and age-associated memory impairment," Front Genet. 5: 419 (2014).
Holmqvist et al., "Kinetic modulation of Kv4-mediated A-current by arachidonic acid is dependent on potassium channel interacting proteins," The Journal of Neuroscience. 21(12): 4154-4161 (2001).
Hool et al., "Redox control of calcium channels: from mechanisms to therapeutic opportunities," Antioxid Redox Signal. 9(4): 409-35 (2007).
Hornak et al., "Face and voice expression identification in patients with emotional and behavioural changes following ventral frontal lobe damage," Neuropsychologia. 34(4): 247-61 (1996).

International Search Report and Written Opinion for International Patent Application No. PCT/IB2018/055348, dated Dec. 11, 2018 (11 pages).
Jaeggi et al., "Improving fluid intelligence with training on working memory," Proc Natl Acad Sci U S A. 105(19): 6829-33 (2008).
Jain et al., "The accumulation of malonyldialdehyde, an end product of membrane lipid peroxidation, can cause potassium leak in normal and sickle red blood cells," Biochemical Medicine and Metabolic Biology. 42(1): 60-65 (1989).
Kagan et al., "Tocopherol stabilizes membrane against phospholipase A, free fatty acids, and lysophospholipids," Ann N Y Acad Sci. 570: 121-35 (1989).
Keller et al., "Evidence of increased oxidative damage in subjects with mild cognitive impairment," Neurology. 64(7): 1152-1156 (2005).
Kim et al., "Cerebral cortical phospholipase A2 activity of senescence-accelerated mouse is increased in an age-dependent manner," Neuroscience research. 29: 269-272 (1997).
Klein et al., "Semantic power measured through the interference of words with color-naming," The American Journal of Psychology, vol. 77(4): 576-588 (1964).
Kumar et al., "Effect of Centella asiatica on cognition and oxidative stress in an intracerebroventricular streptozotocin model of Alzheimer's disease in rats," Clin Exp Pharmacol Physiol. 30(5-6): 336-42 (2003).
Kumar et al., "Physiological and biochemical effects of 17beta estradiol in aging female rat brain," Experimental gerontology. 46: 597-605 (2011).
Lee et al., "Phospholipases A2 and neural membrane dynamics: implications for Alzheimer's disease," J Neurochem. 116(5): 813-819 (2011).
Liebier et al., "Antioxidant protection of phospholipid bilayers by alpha-tocopherol. Control of alpha-tocopherol status and lipid peroxidation by ascorbic acid and glutathione," J Biol Chem. 261(26): 12114-9(1986).
Liu et al., "Effects of arachidonic acid on unitary calcium currents in rat sympathetic neurons," J Physiol. 525 Pt 2(Pt 2): 391-404 (2000).
Lopez et al., "Oxidative stress in Alzheimer's disease and mild cognitive impairment with high sensitivity and specificity," Journal of Alzheimer's Disease. 33: 823-829 (2013).
Low et al., "Effects of daily iron supplementation in primary-school-aged children: systematic review and meta-analysis of randomized controlled trials," CMAJ. 185(17): E791-E802 (2013).
Markesbery, WR., "Oxidative stress hypothesis in Alzheimer's disease," Free Radic Biol Med. 23(1): 134-47 (1997).
Mattson, M.P., "Calcium and neurodegeneration," Aging Cell. 6(3): 337-50 (2007).
McLean et al., "Role of lipid structure in the activation of phospholipase A2 by peroxidized phospholipids," Lipids. 28(6): 505-9 (1993).
Milner, B., "Visually-guided maze learning in man: effects of bilateral hippocampal, bilateral frontal, and unilateral cerebral lesions," Neuropsychologia. 3(4): 317-338 (1965).
Mintel, "Dietary supplement capsules for ages 30-55," http://www.gnpd.com, retrieved on Oct. 4, 2018 (5 pages).
Mintel, "Dietary supplement capsules for ages 55+," http://www.gnpd.com, retrieved on Oct. 4, 2018 (5 pages).
Mishra, Training sensory signal-to-noise resolution in children with ADHD in a global mental health setting, Transl Psychiatry. 6(4): e781 (2016).
Mukherjee et al., "Lysosomal membrane stabilization by alpha-tocopherol against the damaging action of Vipera russelli venom phospholipase A2," Cell Mol Life Sci. 53(2): 152-5 (1997).
Muralikrishna et al., "Phospholipase A2, reactive oxygen species, and lipid peroxidation in cerebral ischemia," Free Radic Biol Med. 40(3): 376-87 (2006).
Nigam et al., "Phospholipase A(2)s and lipid peroxidation," Biochim Biophys Acta. 1488(1-2): 167-81 (2000).
Powell et al., "Assessment of brain impairment with the Rey auditory verbal learning test: a comparison with other neuropsychological measures," Arch Clin Neuropsychol. 6(4): 241-9 (1998).
Rastogi et al., "Ginseng: a promising neuroprotective strategy in stroke," Front Cell Neurosci. 8(457): 1-13 (2015).

(56) References Cited

OTHER PUBLICATIONS

Rudel et al., "Relation of forward and backward digit repetition to neurological impairment in children with learning disabilities," Neuropsychologia. 12:109-118 (1974).
Ruffmann et al., "GSH rescue by N-acetylcysteine," Klin Wochenschr. 69(18): 857-862 (1991).
Ruppersberg et al., "Cloned neuronal I,(A) channels reopen during recovery from inactivation," Nature 353:657-660 (1991).
Sanchez-Mejia et al., "Phospholipase A2 and arachidonic acid in Alzheimer's disease," Biochimica et biophysica acta. 1801: 784-790 (2010).
Scattergood, G. "Singapore start-up Senescence targets younger demographic with new cognitive health supplement," https://www.nutraingredients-asia.com/Article/2017/04/19/Singapore-start-up-Senescence-targets-younger-demographic-with-new-cognitive-health-supplement, retrieved Oct. 31, 2018 (1 page).
Schmitt et al., "Modulation of neuronal calcium channels by arachidonic acid and related substances," J Membr Biol. 145(3): 233-44 (1995).
Sevanian et al., "Phospholipase A2 dependent release of fatty acids from peroxidized membranes," J Free Radic Biol Med. 1(4): 263-71 (1985).
Sevanian et al., "The influence of phospholipase A2 and glutathione peroxidase on the elimination of membrane lipid peroxides," Arch Biochem Biophys. 223(2): 441-52 (1983).
Snyder, H.R., "Major depressive disorder is associated with broad impairments on neuropsychological measures of executive function: a meta-analysis and review," Psychol Bull. 139(1): 81-132 (2013).
Spiteller, G, "The important role of lipid peroxidation processes in aging and age dependent diseases," Mol Biotechnol 37: 5-12 (2007).
Stevens et al., "Acrolein: sources, metabolism, and biomolecular interactions relevant to human health and disease," Molecular nutrition & food research. 52: 7-25 (2008).
Stroop, J. R., "Studies of interference in serial verbal reactions," Journal of experimental psychology. 18(6): 643-62 (1935).
Sultana et al., "Role of oxidative stress in the progression of Alzheimer's disease," J Alzheimers Dis. 19(1): 341-53 (2010).
Sweet, L. H., "N-Back Paradigm," Encyclopedia of Clinical Neuropsychology. 94: 1718-1719 (2011).
Tan et al., "Inhibition of microsomal lipid peroxidation by glutathione and glutathione transferases B and AA. Role of endogenous phospholipase A2," Biochem J. 220(1): 243-52 (1984).
Tejasvi et al., "REVIVE is a daily supplement to combat age-related cognitive decline," Biospectrum (2017) (3 pages).
Terman A., "Garbage catastrophe theory of aging: imperfect removal of oxidative damage?" Redox Rep. 6(1): 15-26 (2001).
Terman et al., "Oxidative stress, accumulation of biological 'garbage', and aging," Antioxid Redox Signal. 8(1-2): 197-204 (2006).
Uzayisenga et al., "Anti-diabetic potential of Panax notoginseng saponins (PNS): a review," Phytother Res. 28(4): 510-6 (2014).
Vaillancourt et al., "4-Hydroxynonenal induces apoptosis in human osteoarthritic chondrocytes: the protective role of glutathione-S-transferase," Arthritis Res Ther. 10(5): R107 (2008).
Villarroel et al., "Inhibition of the Kv4 (Shal) family of transient K+ currents by arachidonic acid," J Neurosci. 16(8): 2522-2531 (1996).
Watson et al., "Diminishing glutathione availability and age-associated decline in neuronal excitability," Neurobiology of Aging. 35: 1074-1085 (2014).
Watson et al., "Failure of delayed nonsynaptic neuronal plasticity underlies age-associated long-term associative memory impairment," BMC Neurosci. 13: 103 (2012).
Watson et al., "Phospholipase A2: the key to reversing long-term memory impairment in a gastropod model of aging," Neurobiology of Aging. 34: 610-620 (2013).
Watson et al., "Redox agents modulate neuronal activity and reproduce physiological aspects of neuronal aging," Neurobiology of Aging. 33: 149-161 (2012).
Watson, Shawn N., "Lipid Peroxidation as an Exponent of Neuronal Senescence," Ph.D. Thesis. University of Calgary: Canada (2013).
Whalley et al., "Cognitive reserve and the neurobiology of cognitive aging," Ageing Res Rev. 3(4): 369-82 (2004).
Xia et al., "Anti-tumor activity of three novel derivatives of ginsenoside on colorectal cancer cells," Steroids. 80:24-9 (2014).
Xie et al., "Glutathione transferase protects neuronal cultures against four hydroxynonenal toxicity," Free Radical Biology & Medicine. 25(8): 979-988 (1998).
Yu et al., "Antioxidative effect of ginseng stem-leaf saponins on oxidative stress induced by cyclophosphamide in chickens," Poult Sci. 94(5): 927-33 (2015).
Yu et al., "Effect of age-related lipid peroxidation on membrane fluidity and phospholipase A2: modulation by dietary restriction," Mech Ageing Dev. 65(1): 17-33 (1992).
Zhu et al., "Age-related changes in glutathione and glutathione-related enzymes in rat brain," Brain Res. 1090(1): 35-44 (2006).
Zuk et al., "Behavioral and neural correlates of executive functioning in musicians and non-musicians," PloS One. 9(6): e99868 (2014).
Sanchez-Mejia et al., "Phospholipase A2 reduction ameliorates cognitive deficits in a mouse model of Alzheimer's disease," Nat Neurosci. 11(11): 1311-8 (2008).
Berry et al., "Rey-Osterrieth complex figure: psychometric characteristics in a geriatric sample," The Clinical Neuropsychologist. 5(2):143-53 (1991) (12 pages).

* cited by examiner

COMPOSITIONS AND METHODS FOR THE TREATMENT AND PREVENTION OF COGNITIVE DECLINE AND PRESERVATION OF NEURONAL FUNCTION

FIELD OF THE INVENTION

The invention relates to compounds, compositions and methods for treating cognitive decline. The invention also relates to compounds, compositions and methods for preserving neuronal function.

BACKGROUND

Neurological decline associated with non-pathological aging is fast becoming a primary concern of Eastern and Western societies as we are beginning to feel the social, monetary and emotional pressures of an aging population. It is evident that the aging nervous system, whether invertebrate or vertebrate, suffers from a progressive deterioration of plastic components, most noticeably that of learning and memory. While this process likely has a diverse and multifactorial cellular and molecular foundation, one of the foremost mechanistic explanations is captured within the Free Radical Theory of Aging. The theory postulates that aging is the result of progressive pro-oxidative shifts in cellular redox states and consequential oxidation-dependent alterations in cell physiology.

While aging is the strongest predictor of numerous pathologies, some of which result in neuronal failure and atrophy, the fact remains that neuronal aging and cognitive decline are also observed in non-pathological iterations of aging. A large body of evidence indicates that oxidative stress is a prominent feature of both pathological and non-pathological forms of nervous system aging.[1-12] If left unchecked, pro-oxidative shifts in cellular-redox states may cause cumulative damage and dysfunction to a variety of structures and processes within the cell, including the plasma membrane.[8-10, 13-15] Neurons, and in particular neuronal membranes, are highly susceptible to non-enzymatic lipid peroxidation, a form of radical attack, due to their post mitotic nature, high oxygen consumption, and elevated levels of poly-unsaturated fatty acids.[13]

In further embodiments, the double bonds responsible for the unsaturation in lipids provide a means through which single electrons can become delocalized across 3 carbons. This facilitates a carbon centered free radical to form on the bis-allylic hydrogen.[16, 17] Due to the high concentration of molecular oxygen within neuronal membranes, the carbon centered free radical may quickly react to form a lipid peroxide radical within the hydrophobic domain of the bilayer. The negative charge on this peroxide may cause the acyl chain to migrate towards the surface (hydrophilic zone) of the bilayer. Movement of the acyl chain to the hydrophilic area may cause an increase in membrane rigidity as the ability of the phospholipids to move within and across layers becomes impaired. Thus, elevated levels of peroxidation may result in increased rigidity of the membrane, a phenomenon observed within both experimentally oxidized membranes as well as aged neuronal membranes.[2, 18, 19] It is thought that due to the reactivity of the lipid peroxide, the radical can also go on to attack an adjacent poly-unsaturated fatty acid, thus starting what is known as a lipid peroxidation chain reaction.

Lipid peroxidation can lead to the production of deleterious lipid metabolites such as 4-hydroxynonenal (4-HNE), malondialdehyde (MDA), lipofuscin and many others.[8, 20-22] The build-up, and improper clearance of these and other pro-inflammatory metabolites has been observed in non-pathological neuronal aging, as well as implicated as a major factor related to the cognitive impairment associated with pathological neuronal diseases(s).[22-28] A critical step linking membrane lipid peroxidation and the production of deleterious metabolites is the liberation of fatty acids from the membrane via the activity of phospholipase $A_2$ ($PLA_2$).

Following lipid peroxidation, $PLA_2$ is thought to function as a repair mechanism through the excision of oxidized fatty acids at the sn-2 position of phospholipids. Liberated fatty acids may then undergo glutathione-mediated reduction and consequential reincorporation into the membrane, if adequate reducing power is available, or remain as a per-oxidized fatty acid.[7, 9, 16, 29-31] An up-regulation of $PLA_2$ has been shown to be a critical component in age-related neuronal changes in both pathological and non-pathological iterations of aging.[5, 6, 10]

Of great interest, separate lines of research have shown free fatty acids can significantly alter (electro)physiological aspects of neuron(s) and network level functionalities through a variety of mechanisms.[32-36] Free fatty acids have been shown to cause significant reductions in neuronal excitability primarily through alterations to both $K^+$ and $Ca^{2+}$ currents. In regards to $K^+$, studies have found substantial free fatty acid effects on rectifying $K^+$ currents, including those intricately linked to age-related changes in cellular excitability, like the $I_A$ current ascribed to the fast-inactivating Kv4 $K^+$ channels.[32-36] Direct interactions involving the association of fatty acids with the inner cavity have been shown to result in a rapid inactivation of sustained $K^+$ currents.[32, 37] Other studies show that peroxidized free fatty acids can function as oxidants and cause redox-related changes to cysteine residues within ion channels.[33, 38] Irrespective of target, slow, rapid and non-inactivating $K^+$ currents have all been shown to be modulated by free fatty acids, some of which have also been closely linked to synaptic plasticity, including long term potentiation induction.[35]

Fatty acids have also been shown to have a substantial capacity to inhibit low voltage activated $Ca^{2+}$ channels (T-Type).[35, 39, 40] These types of channels are key contributors to resting membrane potential and action potential generation, both important aspects of neuronal excitability control. Moreover, free fatty acids have been shown to have strong inhibitory effects on N-type $Ca^{2+}$ channels, the primary channels responsible for pre-synaptic depolarization and neurotransmitter-related synaptic communication.[41] It quickly becomes apparent that the neuromodulatory capabilities of free fatty acids are far reaching and can have significant consequences for neuronal (electro) physiology. If perturbed, the overwhelming amount of evidence may imply a substantive role for lipid peroxidation, $PLA_2$ activation and functional changes to the aging brain.

To date there are no comprehensive treatments specifically designed to ameliorate the deleterious consequences of age and/or lipid (per)oxidation-related changes in neuronal function. More specifically, no treatments are available which target the mechanism after the initial oxidative insult has occurred. There is a need in the art to identify compounds, compositions and methods for preventing cognitive decline and preserving neuronal function.

A further summary of the state of the art is provided by the references described herein and throughout.

SUMMARY OF THE INVENTION

In an embodiment of the present invention, there is provided a composition comprising:

a phospholipase $A_2$ inhibitor;
a lipophilic antioxidant;
a glutathione peroxidase enhancer; and
a glutathione level enhancer.

In a further embodiment of the composition or compositions as outlined above, the phospholipase $A_2$ inhibitor is *Centella asiatica* or an extract thereof, *Ginseng* or an extract thereof, or a combination thereof.

In a further embodiment of the composition or compositions as outlined above, *Centella asiatica* or an extract thereof is a *Centella asiatica* aqueous extract containing asiaticoside, or a *Centella asiatica* extract that inhibits phospholipase $A_2$.

In another embodiment of the composition or compositions as outlined above, the lipophilic antioxidant is tocopherol or a tocopherol derivative.

In another embodiment of the composition or compositions as outlined above, the tocopherol derivative is α-tocopherol succinate.

In another embodiment of the composition or compositions as outlined above, the glutathione peroxidase enhancer is *Ginseng* or an extract thereof, selenocysteine, selenium, cystein or a combination thereof.

In another embodiment of the composition or compositions as outlined above, *Ginseng* or an extract thereof is *Ginseng* root, Asian *Ginseng* root, or an extract of *Ginseng* which comprises one or more compounds that are glutathione peroxidase enhancers.

In another embodiment of the composition or compositions as outlined above, the glutathione level enhancer is α-lipoic acid.

In an embodiment of the present invention, there is provided a composition comprising:
*Centella asiatica* or an extract thereof;
α-tocopherol or a derivative thereof;
*Ginseng* or an extract thereof;
selenocysteine; and
α-lipoic acid.

In a further embodiment of the present invention, there is provided a composition comprising:
*Centella asiatica* aqueous extract;
α-tocopherol succinate;
Asian *Ginseng* aqueous extract;
selenocysteine; and
α-lipoic acid.

In another embodiment of the composition or compositions as outlined above, the amount of the phospholipase $A_2$ inhibitor is from about 1 mg to about 10 g.

In another embodiment of the composition or compositions as outlined above, the amount of the glutathione peroxidase enhancer is from about 1 mg to about 10 g.

In another embodiment of the composition or compositions as outlined above, the amount of the lipophilic antioxidant is from about 0.001 mg to about 10 g.

In another embodiment of the composition or compositions as outlined above, the amount of the glutathione level enhancer is from about 1 mg to about 10 g.

In another embodiment of the composition or compositions as outlined above, the amount of *Centella asiatica* or an extract thereof is from about 1 mg to about 10 g.

In another embodiment of the composition or compositions as outlined above, the amount of α-tocopherol or a derivative thereof is from about 1 mg to about 10 g.

In another embodiment of the composition or compositions as outlined above, the amount of *Ginseng* or an extract thereof is from about 1 mg to about 10 g.

In another embodiment of the composition or compositions as outlined above, the amount of selenocysteine is from about 0.001 to about 10 mg.

In another embodiment of the composition or compositions as outlined above, the amount of α-lipoic acid is from about 1 mg to about 10 g.

In a further embodiment of the composition or compositions as outlined above, the ratio of *Centella asiatica* or an extract thereof:α-tocopherol or a derivative thereof:*Ginseng* or an extract thereof:selenocysteine: α-lipoic acid is about 5000-10000:3000-7000:5000-10000:1-5:1000-6000 by weight.

In yet a further embodiment of the composition or compositions as outlined above, the ratio of *Centella asiatica* or an extract thereof:α-tocopherol or a derivative thereof:*Ginseng* or an extract thereof:selenocysteine: α-lipoic acid is about 7840:4900:7840:1:2960 by weight.

In an embodiment of the composition or compositions as outlined above, the composition provides a synergistic effect on the treatment of cognitive decline compared to the treatment of cognitive decline with the individual components of the composition.

In a further embodiment of the composition or compositions as outlined above, *Centella asiatica* or an extract thereof is from about 10 to about 50% w/w of the composition.

In a further embodiment of the composition or compositions as outlined above, α-tocopherol is from about 10 to about 30% w/w of the composition.

In a further embodiment of the composition or compositions as outlined above, *Ginseng* or an extract thereof is from about 10 to about 50% w/w of the composition.

In a further embodiment of the composition or compositions as outlined above, selenocysteine is from about 0.0001 to about 0.001% w/w of the composition.

In a further embodiment of the composition or compositions as outlined above, α-lipoic acid is from about 1 to about 40% w/w of the composition.

In an embodiment of the present invention, there is provided a method for preserving, improving or increasing neuronal function in a neuronal cell by treating the neuronal cell with the composition.

In a further embodiment of the present invention, there is provided a method for treating or preventing cognitive decline in a subject in need thereof by administering the composition.

In a further embodiment of the method or methods as outlined above, the cognitive decline is normal age-related cognitive decline.

In yet a further embodiment of the method or methods as outlined above, the cognitive decline is loss of cognitive function, loss of memory, memory impairment, loss of short term memory, loss of intermediate term memory, loss of long term memory or loss of an ability to learn, store or recall information, loss of attention span, loss of language skills, loss of writing skills, loss of problem solving skills, loss of spatial processing, loss of focus, loss of emotional recognition accuracy/speed, loss of executive function accuracy/speed, or any combination thereof.

In yet a further embodiment of the method or methods as outlined above, the cognitive decline is from Alzheimer's disease, Lewy body dementia, vascular dementia, Parkinson's disease-associated dementia, Huntington's disease-associated dementia, AIDS-associated dementia, benign senile forgetfulness, Down's syndrome-associated dementia, multi-infarct dementia, multiple sclerosis, tardive dyskinesia, Wernicke-Korsakoff syndrome or alcoholism-associated dementia.

In an embodiment of the method or methods as outlined above, the composition is administered to the subject simultaneously, sequentially or in combination with a pharmacological agent.

In another embodiment of the method or methods as outlined above, the pharmacological agent is for the treatment of Alzheimer's disease, Lewy body dementia, vascular dementia, Parkinson's disease-associated dementia, Huntington's disease-associated dementia, AIDS-associated dementia, benign senile forgetfulness, Down's syndrome-associated dementia, multi-infarct dementia, multiple sclerosis, tardive dyskinesia, Wernicke-Korsakoff syndrome or alcoholism-associated dementia.

In an embodiment of the method or methods as outlined above, the method further comprises:
a) selecting a subject with suspected cognitive decline or at risk of cognitive decline; and
b) administering the composition to the subject.

In a further embodiment of the method or methods as outlined above, the method further comprises performing cognitive testing of the subject after administering the composition.

In an embodiment of the present invention, there is provided a method for preserving or improving neuronal function in a subject in need thereof by administering the composition to a neuron or neuronal cells in vitro or to a subject in vivo.

In another embodiment of the present invention, there is provided an oral formulation of the composition that comprises from about 1 mg to about 10 g phospholipase $A_2$ inhibitor, from about 1 mg to about 10 g lipophilic antioxidant, from about 0.001 mg to about 10 g glutathione peroxidase enhancer and from about 1 mg to about 10 g glutathione level enhancer.

In yet another embodiment of the present invention, there is provided an oral formulation of the composition that comprises about 200 mg phospholipase $A_2$ inhibitor, about 125 mg lipophilic antioxidant, about 200 mg glutathione peroxidase enhancer and about 76 mg glutathione level enhancer.

In yet a further embodiment of the present invention, there is provided an oral formulation of the composition that comprises from about 1 mg to about 10 g *Centella asiatica* or an extract thereof, from about 1 mg to about 10 g α-tocopherol or a derivative thereof, from about 1 mg to about 10 g *Ginseng* or an extract thereof, from about 0.001 mg to about 1 g selenocysteine and from about 1 mg to about 10 g α-lipoic acid.

In yet a further embodiment of the present invention, there is provided an oral formulation of the composition that comprises about 200 mg *Centella asiatica* or an extract thereof, about 125 mg α-tocopherol or a derivative thereof, about 200 mg *Ginseng* or an extract thereof, about 0.0255 mg selenocysteine and about 75.76 mg α-lipoic acid.

In an embodiment of the method or methods as outlined above, the composition is in the form of a pill, capsule, liquid, syrup, powder, cream, ointment, gel, or paste.

In an embodiment of the method or methods as outlined above, the composition is for daily administration.

In an embodiment of the present invention, the composition is a food product comprising the composition.

In an embodiment of the food product or products as outline above, the composition is incorporated into, but not limited to an energy bar, oatmeal, cereal or yogurt.

In an embodiment of the present invention, the composition is a beverage product comprising the composition.

In an embodiment of the beverage product or products as outline above, the composition is incorporated into, but not limited to an energy shake, smoothie, tea, coffee or flavoured water.

In a further embodiment of the present invention, there is provided a composition comprising: *Centella asiatica* or an extract thereof, α-tocopherol or a derivative thereof, *Ginseng* or an extract thereof, a selenium compound, and α-lipoic acid. Preferably, the composition comprises *Centella asiatica* extract which comprises about 20% asiaticosides, d-α-tocopherol succinate; *Ginseng* root extract comprising about 5% ginsenosides; L-selenomethionine; and α-lipoic acid. In a more preferred embodiment, the composition is in a unit dosage form comprising about 25-200 mg α-lipoic acid, about 10-50 mcg selenomethionine, about 40-200 mg d-α-tocopherol succinate, about 20-80 mg asiaticosides derived from *Centella asiatica* extract, and about 4-20 mg ginsenosides derived from *Ginseng* root extract. In yet a more preferred embodiment the composition is in a unit dosage form comprising about 50 mg or 100 mg lipoic acid, about 25 mcg L-selenomethionine, about 83 mg or 125 mg d-α-tocopherol succinate, about 200 mg or 175 mg *Centella asiatica* whole plant extract providing about 40 mg or 35 mg asiaticosides, respectively; and 175 mg or 150 mg *Panax Ginseng* extract comprising about 8.75 mg and 7.5 mg ginsenosides, respectively.

It is further contemplated that the compositions or formulations as described herein and throughout may further comprise one or more pharmaceutically acceptable excipients, for example, but not limited to microcrystalline cellulose, magnesium stearate, silicon dioxide or a combination thereof. Other excipients also may be included.

The present invention also provides a composition or formulation as described herein and throughout for use in improving cognitive function or treating and/or preventing cognitive decline in a subject in need thereof.

Also contemplated by the present invention is a method for treating or preventing cognitive decline in a subject in need thereof by administering a composition or formulation as described herein and throughout to the subject. The cognitive decline may be normal age-related cognitive decline, for example, but not limited to loss of cognitive function, loss of memory, memory impairment, loss of short term memory, loss of intermediate term memory, loss of long term memory or loss of an ability to learn, store or recall information, loss of attention span, loss of language skills, loss of writing skills, loss of problem solving skills, loss of spatial processing, loss of focus, loss of emotional recognition accuracy/speed, loss of executive function accuracy/speed, or any combination thereof.

In a further embodiment, the cognitive decline is from a degenerative disease or disorder, for example, but not limited to Alzheimer's disease, Lewy body dementia, vascular dementia, Parkinson's disease-associated dementia, Huntington's disease-associated dementia, AIDS-associated dementia, benign senile forgetfulness, Down's syndrome-associated dementia, multi-infarct dementia, multiple sclerosis, tardive dyskinesia, Wernicke-Korsakoff syndrome or alcoholism-associated dementia.

In a further embodiment, the composition is as described herein but is not a composition comprising 125 mg (150 IU) d-alpha-tocopherol succinate, 75 mg alpha-lipoic acid, 175 mg *Centella asiatica* whole plant extract comprising 40% asiaticosides, 175 mg *Panax Ginseng* stem and leaves extract comprising 5% ginsenosides and 25 mcg L-selenomethionine.

The present invention also contemplates a method of making any composition or formulation as described herein, for example, but not limited by:

combining d-alpha-tocopherol succinate, alpha-lipoic acid, *Centella asiatica* extract, *Panax ginseng* root extract and L-selenomethionine, wherein *Centella asiatica* extract and *Panax ginseng* root extract are derived from water-ethanol extractions. The method may further comprise packaging the composition in a capsule with microcrystalline cellulose, magnesium stearate and silicon dioxide. However, a variety of other methodologies as is known in the art also may be employed.

DETAILED DESCRIPTION

Figure 1:
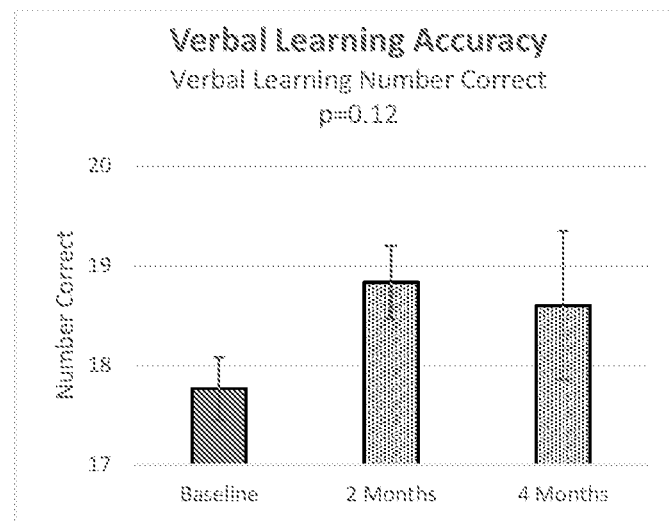
FIG. 1 shows results of verbal learning accuracy tests (verbal learning number correct) on human subjects during clinical trials at baseline and following 2 and 4 months dosing with compositions of the instant invention.

Described herein are embodiments of compositions for preventing cognitive decline and methods for treating cognitive decline. Also described herein are compositions and methods for preserving neuronal function. It will be appreciated that the compositions, methods and embodiments described herein are for illustrative purposes intended for those skilled in the art and are not meant to be limiting in any way. All references to embodiments or examples throughout the disclosure should be considered a reference to an illustrative and non-limiting embodiment or an illustrative and non-limiting example. Further, all statements pertaining to biological mechanisms are not meant to be limiting or bound by theory.

According to an embodiment of the present invention, there is provided a composition for preventing and/or treating cognitive decline, the composition comprising:

a phospholipase $A_2$ inhibitor;
a lipophilic antioxidant;
a glutathione peroxidase enhancer; and
a glutathione level enhancer.

According to a further embodiment of the present invention, there is provided a composition for preserving neuronal function, the composition comprising:
a phospholipase $A_2$ inhibitor;
a lipophilic antioxidant;
a glutathione peroxidase enhancer; and
a glutathione level enhancer.

In the context of the present invention, by the term "a phospholipase A2 inhibitor" it is meant an agent, chemical or protein that reduces, inhibits or suppresses the activity of PLA2. An agent, chemical or protein may be tested for its ability to reduce, inhibit or suppress PLA2 activity in any assay known in the art, for example, but not limited to INVITROGEN™ ENZCHEK® Phospholipase A2 Assay Kit. In this assay, an agent, chemical or protein is considered a PLA2 inhibitor if it reduces the activity of PLA2 by 10 to 100%, for example, but not limited to 10, 20, 30, 40, 50, 60, 70, 80, 90 or 100% when compared to a negative control. One representative example of a PLA2 inhibitor which is not meant to be limiting in any manner is *Centella asiatica*, also known as Gotu kola. It will also be appreciated that an extract of *Centella asiatica* may be used. The extract may be obtained from the aqueous extract, alcohol extract, acetone extract or a combination thereof, of leaves or edible plant parts. The whole plant of *Centella asiatica* can be also used. The extract and whole plant may contain pentacyclic triterpenoids, for example, but not limited to asiaticoside. Other representative examples of PLA2 inhibitors are *Ginseng* or an extract thereof, fatty acid trifluoromethyl ketone, methyl arachidonyl fluorophosphonate, bromoenol lactone, 1,3-disubstituted propan-2-ones polyfluoroalkyl ketones, stearidonic acid, curcumin or an extract thereof, and aristolochic acid.

In the context of the present invention, by the term "lipophilic antioxidant" it is meant an agent, chemical or protein that inhibits the oxidation of membrane lipids. The lipophilic antioxidant also includes a hydrophobic (lipophilic) region, for example, an alkyl chain. An agent, chemical or protein may be tested for its antioxidant activity by any assay known in the art, for example, but not limited to SIGMA-ALDRICH® Antioxidant Assay Kit. In this assay, an agent, chemical or protein is considered an antioxidant if it possesses 10 to 100% antioxidant activity, for example, but not limited to 10, 20, 30, 40, 50, 60, 70, 80, 90 or 100% when compared to a positive control. One representative example of a lipophilic antioxidant is tocopherol. It will be appreciated that tocopherols include natural or synthetic $\alpha$-, $\beta$-, $\gamma$- and $\delta$-tocopherols, with $\alpha$-tocopherol being the most active antioxidant. A derivative of $\alpha$-tocopherol, such as $\alpha$-tocopherol succinate, may also be contemplated.

In the context of the present invention, by the term "a glutathione peroxidase enhancer" it is meant an agent, chemical or protein that enhances or increases the activity of glutathione peroxidase. An agent, chemical or protein may be tested for its ability to enhance or increase glutathione peroxidase activity in any glutathione peroxidase assay known in the art, for example, but not limited to SIGMA-ALDRICH® Glutathione Peroxidase Assay Kit. In this assay, an agent, chemical or protein is considered a glutathione peroxidase enhancer if it increases the activity of glutathione peroxidase by 10 to 100%, for example, but not limited to 10, 20, 30, 40, 50, 60, 70, 80, 90 or 100% when compared to a negative control. One representative example of a glutathione peroxidase enhancer is *Ginseng*. It will be appreciated that *Ginseng* can be obtained from an aqueous extract, alcohol extract or a combination thereof of *Ginseng* root, stem and leaf or the whole plant itself may be used, for example, in a powdered or other form. Other representative examples of glutathione peroxidase enhancers are selenocysteine, selenium and cysteine.

In the context of the present invention, by the term "a glutathione level enhancer" it is meant an agent, chemical or protein that enhances or increases the level of glutathione. An agent, chemical or protein may be tested for its ability to increase glutathione levels in any glutathione assay known in the art, for example, but not limited to Sigma-Aldrich® Glutathione Peroxidase Assay Kit. In preparation for this assay, cells may be incubated with the compound of interest and then lysed in accordance with procedures and methods commonly known in the art. The cell lysate may be used as a substrate in the assay to determine glutathione levels. In this assay, an agent, chemical or protein is considered a glutathione level enhancer if it increases the level of glutathione by 10 to 100%, for example, but not limited to 10, 20, 30, 40, 50, 60, 70, 80, 90 or 100% when compared to a negative control. One representative example of a glutathione level enhancer is $\alpha$-lipoic acid. Another representative example of a glutathione level enhancer is N-acetylcysteine.

In an embodiment, the composition comprises from about 1 to about 10,000 mg of phospholipase $A_2$ inhibitor, for example, but not limited to 1, 10, 20, 50, 100, 200, 300, 400, 500, 1000, 2000, 3000, 4000, 5000, 6000, 7000, 8000, 9000 or 10,000 mg of phospholipase $A_2$ inhibitor. Further, the composition may comprise a range of amounts as defined by any two of the values listed above or any two amounts therein between. In a preferred embodiment, the phospholipase $A_2$ inhibitor is *Centella asiatica* or an extract thereof.

In an embodiment, the composition comprises from about 1 to about 10,000 mg of lipophilic antioxidant, for example, but not limited to 1, 10, 20, 50, 100, 200, 300, 400, 500, 1000, 2000, 3000, 4000, 5000, 6000, 7000, 8000, 9000 or 10,000 mg of lipophilic antioxidant. Further, the composition may comprise a range of amounts as defined by any two of the values listed above or any two amounts therein between. In a preferred embodiment, the lipophilic antioxidant is $\alpha$-tocopherol or a derivative thereof.

In an embodiment, the composition comprises from about 1 to about 10,000 mg of a glutathione peroxidase enhancer, for example, but not limited to 1, 10, 20, 50, 100, 200, 300, 400, 500, 1000, 2000, 3000, 4000, 5000, 6000, 7000, 8000, 9000 or 10,000 mg of a glutathione peroxidase enhancer. Further, the composition may comprise a range of amounts as defined by any two of the values listed above or any two amounts therein between. In a preferred embodiment, the glutathione peroxidase enhancer is *Ginseng* or an extract thereof, selenocysteine or a combination thereof.

In an embodiment, the composition comprises from about 1 to about 10,000 mg of a glutathione level enhancer, for example, but not limited to 1, 10, 20, 50, 100, 200, 300, 400, 500, 1000, 2000, 3000, 4000, 5000, 6000, 7000, 8000, 9000 or 10,000 mg of a glutathione level enhancer. Further, the composition may comprise a range of amounts as defined by any two of the values listed above or any two amounts therein between. In a preferred embodiment, the glutathione level enhancer is $\alpha$-lipoic acid.

In one embodiment, which is not meant to be limiting in any manner, the composition comprises *Centella asiatica* or an extract thereof, $\alpha$-tocopherol or a derivative thereof, *Ginseng* or an extract thereof, selenocysteine and $\alpha$-lipoic acid. Extracts of *Centella asiatica* and *Ginseng* may be performed by water/ethanol extraction via homogenation or by any other suitable solvent system and/or extraction process known in the art. In a preferred embodiment, the extraction process for *Centella asiatica* and *Ginseng* is a water/ethanol extraction process and produces an extract comprising about 20% w/w asiaticosides and about 5% w/w total ginsenosides, respectively when dried. However, the present invention also contemplates embodiments wherein the extraction process results in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40% w/w or higher asiaticosides or ginsenosides when dried. The amount of asiaticosides or ginsenosides may also be defined by a range by any two of the values recited or any numbers therein between.

In an embodiment, the composition comprises from about 1 to about 10,000 mg of *Centella asiatica* or an extract thereof, for example, but not limited to 1, 10, 20, 50, 100, 200, 300, 400, 500, 1000, 2000, 3000, 4000, 5000, 6000, 7000, 8000, 9000 or 10,000 mg of *Centella asiatica* or an extract thereof. Further, the composition may comprise a range of amounts as defined by any two of the values listed above or any two amounts therein between.

In a further embodiment, the composition comprises from about 1 to about 10,000 mg of α-tocopherol or a derivative thereof, for example, but not limited to 1, 10, 20, 50, 100, 200, 300, 400, 500, 1000, 2000, 3000, 4000, 5000, 6000, 7000, 8000, 9000 or 10,000 mg of α-tocopherol or a derivative thereof. Further, the composition may comprise a range of amounts as defined by any two of the values listed or any two amounts therein between.

One embodiment of the composition comprises from about 1 to about 10,000 mg of *Ginseng* or an extract thereof, for example, but not limited to 1, 10, 20, 50, 100, 200, 300, 400, 500, 1000, 2000, 3000, 4000, 5000, 6000, 7000, 8000, 9000 or 10,000 mg of *Ginseng* or an extract thereof. Further, the composition may comprise a range of amounts as defined by any two of the values listed above or any two amounts therein between.

In another embodiment, the composition comprises from about 0.001 to about 0.5 mg of selenocysteine, for example, but not limited to 0.001, 0.005, 0.01, 0.015, 0.02, 0.03, 0.05, 0.07, 0.1, 0.2, 0.3, 0.4 or 0.5 mg of selenocysteine. Further, the composition may comprise a range of amounts as defined by any two of the values listed above or any two amounts therein between. Further, the present invention also contemplates replacing selenocysteine in any passage or composition described herein with selenomethionine and vice-versa unless clearly indicated otherwise.

In general, one embodiment of the composition comprises from about 1 to about 10,000 mg of α-lipoic acid, for example, but not limited to 1, 10, 20, 50, 100, 200, 300, 400, 500, 1000, 2000, 3000, 4000, 5000, 6000, 7000, 8000, 9000 or 10,000 mg of α-lipoic acid. Further, the composition may comprise a range of amounts as defined by any two of the values listed above or any two amounts therein between.

One example of the composition comprises from about 10 to about 50% w/w of *Centella asiatica* or an extract thereof, for example, but not limited to 10, 20, 30, 40 or 50% w/w of *Centella asiatica* or an extract thereof.

Another example of the composition comprises from about 10 to 30% w/w of α-tocopherol or a derivative thereof, for example, but not limited to 10, 20 or 30% w/w of α-tocopherol or a derivative thereof.

Yet another example of the composition comprises from about 10 to 50% w/w of *Ginseng* or an extract thereof, for example, but not limited to 10, 20, 30, 40 or 50% w/w of *Ginseng* or an extract thereof.

A further example of the composition comprises from about 0.0001 to 0.001% w/w of selenocysteine, for example, but not limited to 0.0001, 0.0002, 0.0005, 0.0007 or 0.001% w/w of selenocysteine.

A further example of the composition comprises from about 1 to 40% w/w of α-lipoic acid, for example, but not limited to 1, 2, 5, 7, 10, 20, 30 or 40% w/w of α-lipoic acid.

In an embodiment which is not meant to be limiting, the composition comprises the following ratio of components: *Centella asiatica* or an extract thereof:α-tocopherol or a derivative thereof:*Ginseng* or an extract thereof:selenocysteine: α-lipoic acid of about 5000-10000:3000-7000:5000-10000:1-5:1000-6000 by weight.

In an embodiment which is not meant to be limiting, the composition may comprise the ratio of *Centella asiatica* or an extract thereof:α-tocopherol or a derivative thereof:*Ginseng* or an extract thereof:selenocysteine: α-lipoic acid of about 7840:4900:7840:1:2960 by weight.

It will be appreciated that the phospholipase $A_2$ inhibitor, the lipophilic antioxidant, the glutathione peroxidase enhancer and the glutathione level enhancer are preferably compounds that have no cytotoxicity or low cytotoxicity for cells or humans when the composition comprising these compounds is administered at the dosages described herein.

According to a further embodiment of the present invention, there is provided a method for preserving, improving or increasing neuronal function in a neuronal cell by treating the neuronal cell with the composition as described herein. The neuronal cell may be treated in-vitro or in-vivo.

In the context of the present invention, by the term "neuronal function" it is meant any physiological parameter of normal neuronal activity. This can include but is not limited to: neuronal electrophysiology, synaptic efficacy, neuron shape/size, metabolite composition and/or energy usage. It will be appreciated that neuronal function may be preserved by decreasing lipid peroxidation. Neuronal function also may be preserved by maintaining, increasing or improving neuronal excitability. The increase or preservation of neuronal function can be measured by assessing common metrics used in electrophysiological assessments. These include but are not limited to: action potential frequency and shape, resting membrane potential, membrane resistance and/or rheobase measurements. According to an embodiment of the present invention, there is provided a method for treating or preventing cognitive decline in a subject in need thereof by administering the composition to the subject.

Without wishing to be bound by theory or limiting in any manner, cognitive decline refers to the typical cognitive decline that commonly becomes most apparent in individuals over the age of 40. Cognitive decline in a subject may include varying levels of loss of cognitive function, loss of memory, memory impairment, loss of short term memory, loss of intermediate term memory, loss of long term memory, loss of an ability to learn, store or recall information or loss of spatial processing, loss of focus, loss of emotional recognition accuracy/speed, loss of executive function accuracy/speed, or any combination thereof. These symptoms may occur at a minimal level, commonly associated with the natural aging process, or may occur with more severity as the individual ages.

The symptoms may be determined based on the individual's own experiences. The symptoms may also be observed by family and friends of the individual. Some examples of symptoms that can indicate cognitive decline are, without limitation, forgetfulness, especially for important events such as appointments or social engagements, misplacing objects, losing train of thought or thread of a conversation, book or movie, difficulty in finding words, repeatedly asking the same questions, inability to follow directions, disorientation as to the date or time of day, not recognizing familiar people, feeling overwhelmed by making decisions, having difficulty planning steps to accomplish a task or interpreting instructions, having difficulty finding the way around familiar environments, impulsiveness, showing poor judgment and slowed speed of cognitive processing.

In a further embodiment, it is contemplated that cognitive decline may also be related to a disease state such as, but not limited to, Alzheimer's disease, Lewy body dementia, vascular dementia, Parkinson's disease-associated dementia, Huntington's disease-associated dementia, AIDS-associated dementia, benign senile forgetfulness, Down's syndrome-associated dementia, multi-infarct dementia, multiple sclerosis, tardive dyskinesia, Wernicke-Korsakoff syndrome or alcoholism-associated dementia.

The present invention also provides a method for treating or preventing cognitive decline, the method comprising selecting a subject with suspected cognitive decline or at risk of cognitive decline and administering the composition to the subject. A further embodiment of the method involves testing the subject for cognitive stabilization or improvement, for example, but not limited to solving one or more math questions or the like. The subject may be suspected of having cognitive decline by being evaluated based on the symptoms stated above or the results of cognitive tests. It is appreciated that cognitive decline does not need to be diagnosed by a physician and may be determined by the subject's own experiences.

The present invention also provides a method for preserving neuronal function in a subject by administering the composition to the subject. It is appreciated that improvements and/or preservation of neuronal function may be determined clinically or subjectively by the subject or a person observing the subject over a period of time.

In one embodiment, an oral formulation of the composition may comprise from about 1 mg to about 10 g phospholipase $A_2$ inhibitor, from about 1 mg to about 10 g lipophilic antioxidant, from about 0.001 mg to about 10 g glutathione peroxidase enhancer and from about 1 mg to about 10 g glutathione level enhancer.

In a preferred embodiment, an oral formulation of the composition may comprise, for example, about 200 mg phospholipase $A_2$ inhibitor, about 125 mg lipophilic antioxidant, about 200 mg glutathione peroxidase enhancer and about 76 mg glutathione level enhancer.

In another embodiment, an oral formulation of the composition may comprise from about 1 mg to about 10 g *Centella asiatica* or an extract thereof, from about 1 mg to about 10 g α-tocopherol or a derivative thereof, from about 1 mg to about 10 g *Ginseng* or an extract thereof, from about 0.001 to about 10 mg selenocysteine and from about 1 mg to about 10 g α-lipoic acid.

TABLE 1

| Composition Component | Amount (mg) |
|---|---|
| *Centella asiatica* or an extract thereof | 200.0000 |
| α-Tocopherol or a derivative thereof | 125.0000 |
| Ginseng or an extract thereof | 200.0000 |
| Selenocysteine | 0.0255 |
| α-Lipoic acid | 76 |

In a preferred example as shown in Table 1, an oral formation of the composition may comprise about 200 mg *Centella asiatica* or an extract thereof, about 125 mg α-tocopherol or a derivative thereof, about 200 mg *Ginseng* or an extract thereof, about 0.025 mg selenocysteine and about 76 mg α-lipoic acid. In a further embodiment, the present invention contemplates compositions comprising ±50% variation by weight in any component, for example 1, 2, 5, 7, 10, 15, 20, 25, 30, 35, 40, 45 or 50% variation by weight.

It will be appreciated that the composition may be in the form of a pill, capsule, liquid, syrup, powder, cream, ointment, gel, paste, or any other formulation which will enable the delivery of the composition for example, but not limited to, into the body of the subject.

In one embodiment, a dose of the composition may be taken once a day or more, for example, 1, 2, 3, 4, 5, 6, 7, 8, 9 or 10 times daily. Doses of the composition taken at different times of the day may be in the same or varying amounts. Without being limiting, an example of a dosing schedule may be a dose of 0.5 g in the morning, a dose of 0.25 g at lunch and a dose of 1 g in the evening. In a preferred embodiment, which is not meant to be limiting, the composition is taken daily.

It is also contemplated that a food or beverage product may comprise the composition as described herein. For example, the composition may be incorporated into, for example, energy bars, oatmeal, cereal or yogurt. The composition may also be incorporated into beverages, for example, protein shakes, smoothies, tea, coffee, sports drinks or flavoured water.

Example 1

Figure 2:
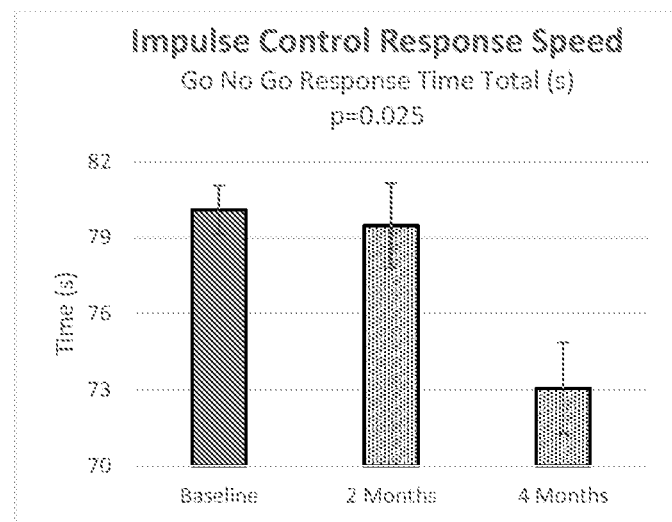
FIG. 2 shows results of impulse control response speed tests (go-no-go response time totals) on human subjects during clinical trials at baseline and following 2 and 4 months dosing with compositions of the instant invention.
Figure 3:
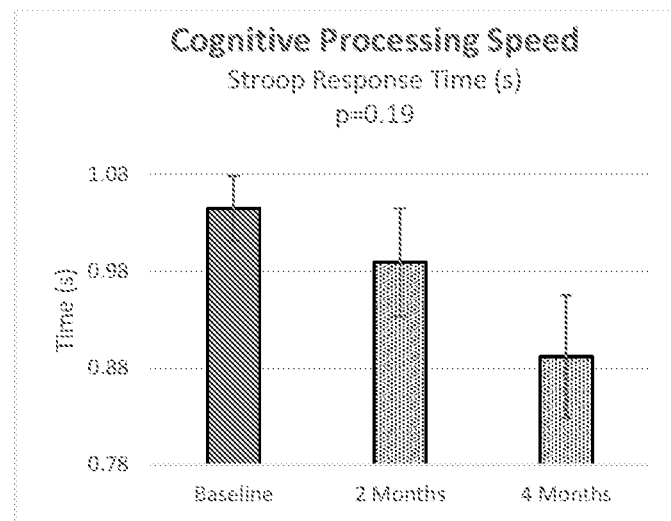
FIG. 3 shows results of cognitive processing speed tests (Stroop response times) on human subjects during clinical trials at baseline and following 2 and 4 months dosing with compositions of the instant invention.
Figure 4:
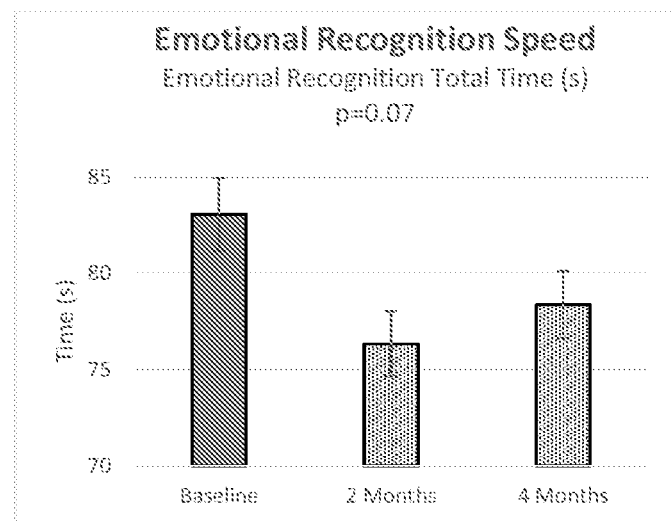
FIG. 4 shows results of emotional recognition speed tests (emotional recognition time totals) on human subjects during clinical trials at baseline and following 2 and 4 months dosing with compositions of the instant invention.
Figure 5:
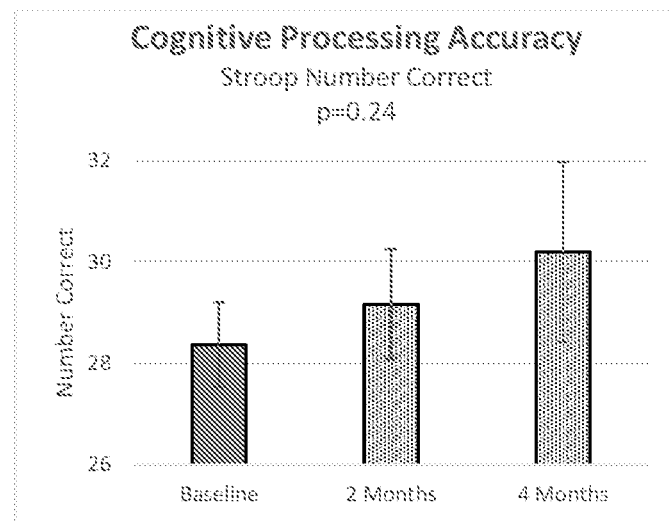
FIG. 5 shows results of cognitive processing accuracy tests (Stroop number correct) on human subjects during clinical trials at baseline and following 2 and 4 months dosing with compositions of the instant invention.
Figure 6:
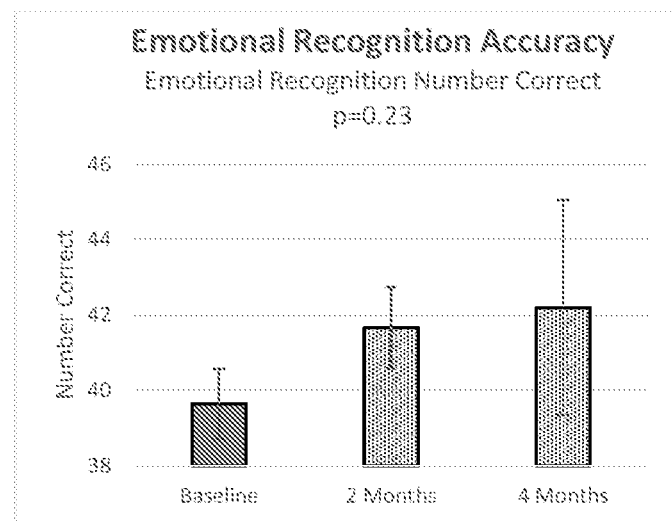
FIG. 6 shows results of emotional recognition accuracy tests (emotional recognition number correct) on human subjects during clinical trials at baseline and following 2 and 4 months dosing with compositions of the instant invention.
Figure 7:
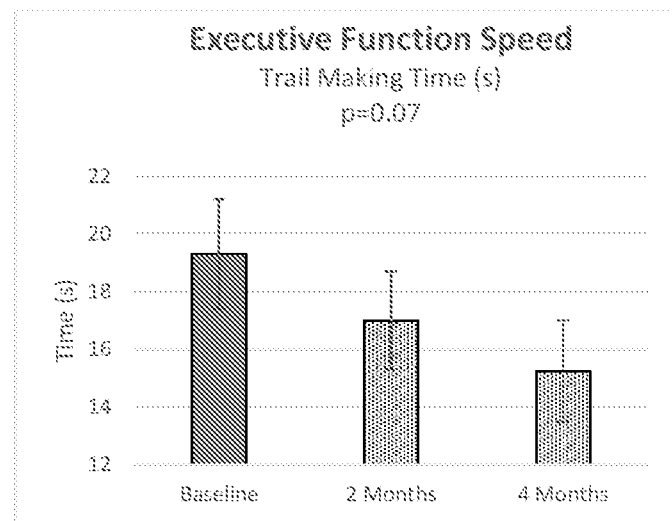
FIG. 7 shows results of executive function speed tests (trail making times) on human subjects during clinical trials at baseline and following 2 and 4 months dosing with compositions of the instant invention.
Figure 8:
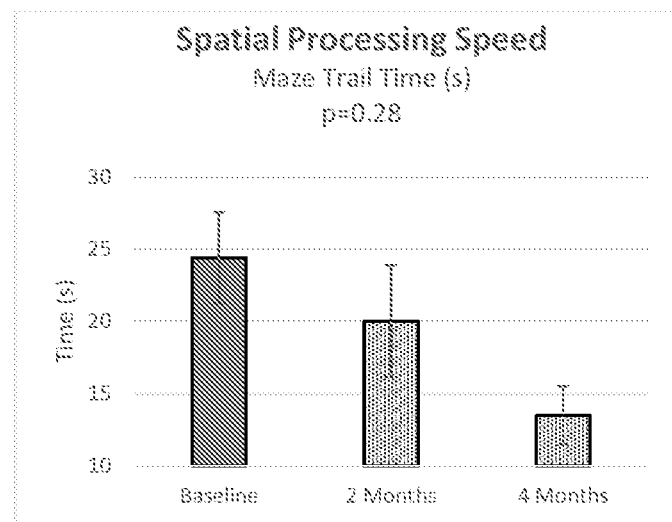
FIG. 8 shows results of spatial processing speed tests (maze trail times) on human subjects during clinical trials at baseline and following 2 and 4 months dosing with compositions of the instant invention.
Figure 9:
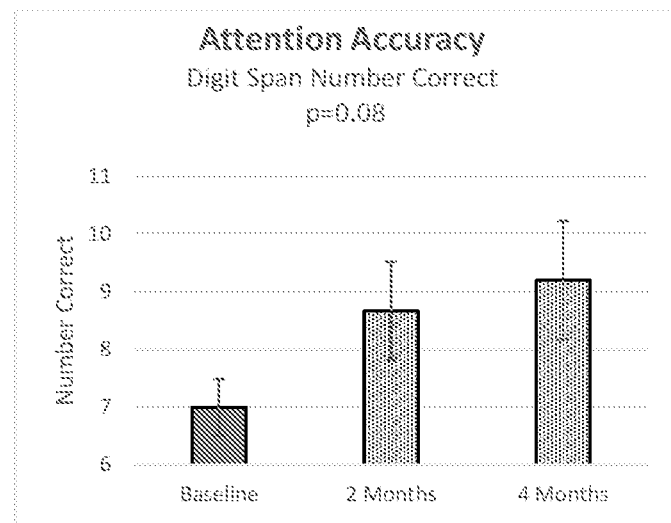
FIG. 9 shows results of attention accuracy tests (digit span number correct) on human subjects during clinical trials at baseline and following 2 and 4 months dosing with compositions of the instant invention.
Figure 10:
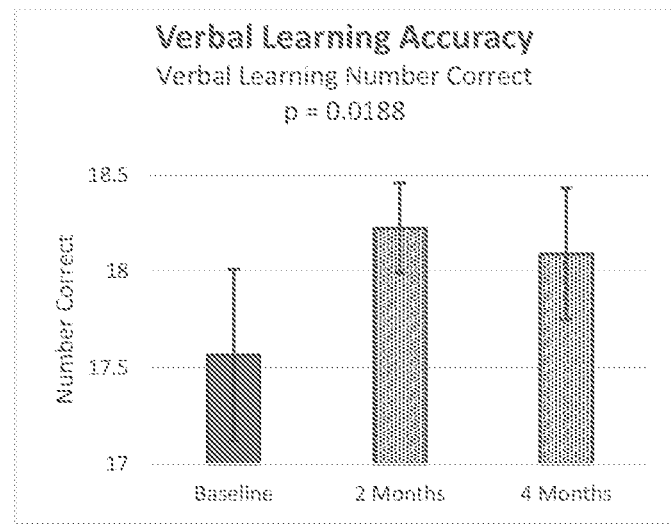
FIG. 10 shows results of verbal learning accuracy tests (verbal learning number correct) on human subjects during clinical trials at baseline and following 2 and 4 months dosing with compositions of the instant invention.
Figure 11:
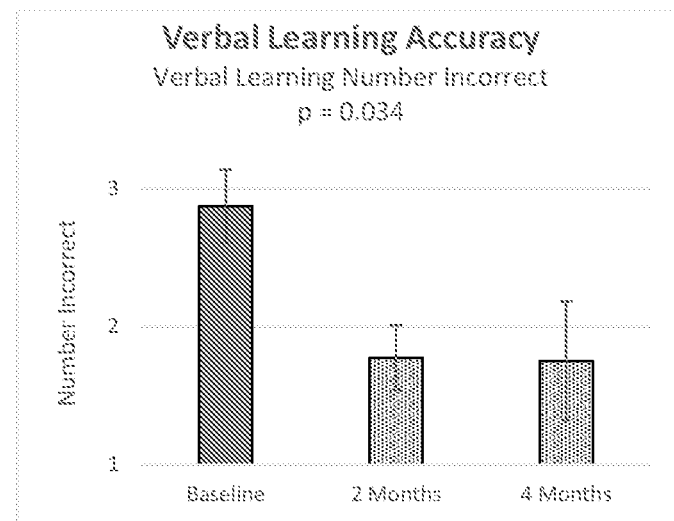
FIG. 11 shows results of verbal learning accuracy tests (verbal learning number incorrect) on human subjects during clinical trials at baseline and following 2 and 4 months dosing with compositions of the instant invention.
Figure 12:
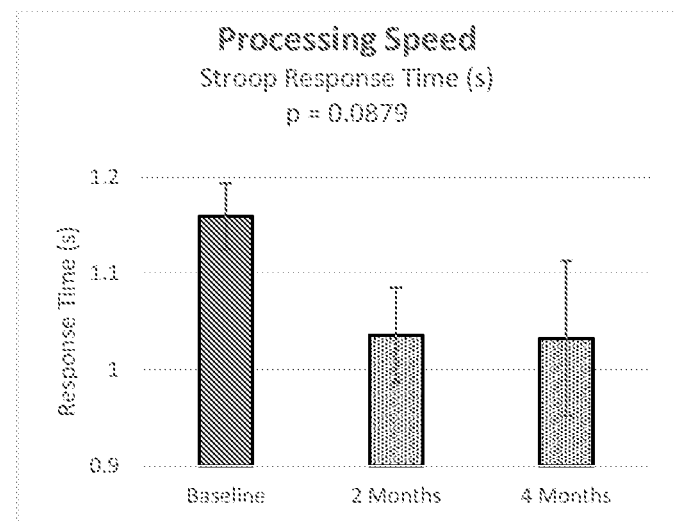
FIG. 12 shows results of processing speed tests (Stroop response times) on human subjects during clinical trials at baseline and following 2 and 4 months dosing with compositions of the instant invention.
Figure 13:
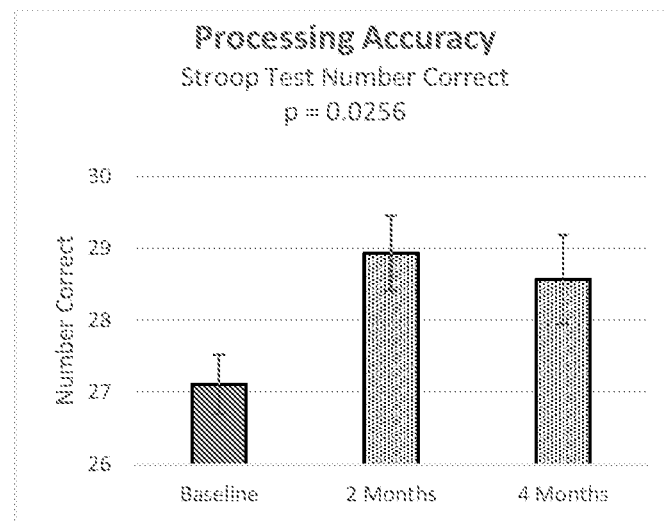
FIG. 13 shows results of processing accuracy tests (Stroop test number correct) on human subjects during clinical trials at baseline and following 2 and 4 months dosing with compositions of the instant invention.
Figure 14:
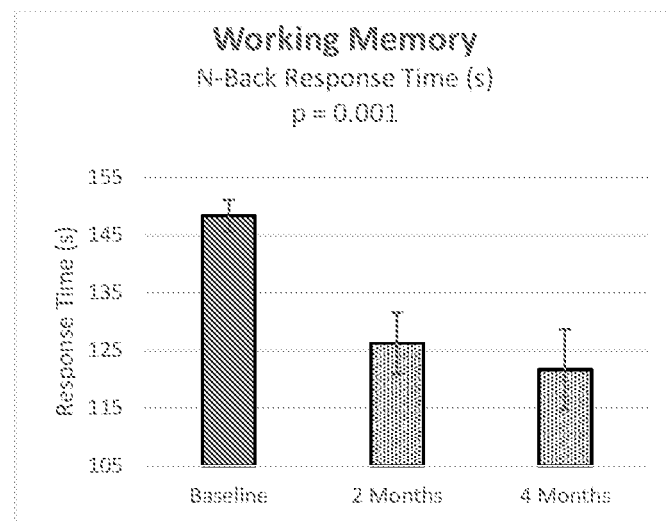
FIG. 14 shows results of working memory tests (N-Back response total times) on human subjects during clinical trials at baseline and following 2 and 4 months dosing with compositions of the instant invention.
Figure 15:
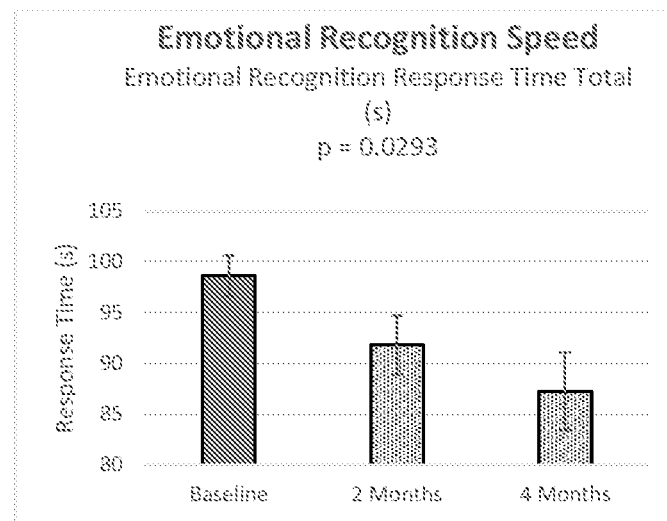
FIG. 15 shows results of emotional recognition speed tests (emotional recognition response total times) on human subjects during clinical trials at baseline and following 2 and 4 months dosing with compositions of the instant invention.
Figure 16:
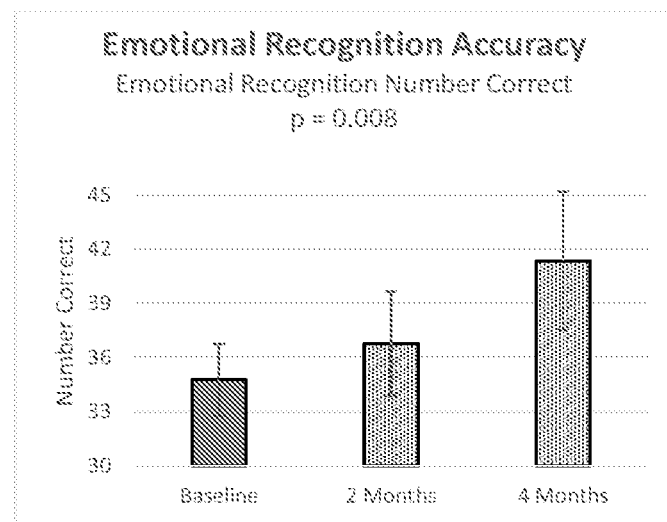
FIG. 16 shows results of emotional recognition accuracy tests (emotional recognition number correct) on human subjects during clinical trials at baseline and following 2 and 4 months dosing with compositions of the instant invention.
Figure 17:
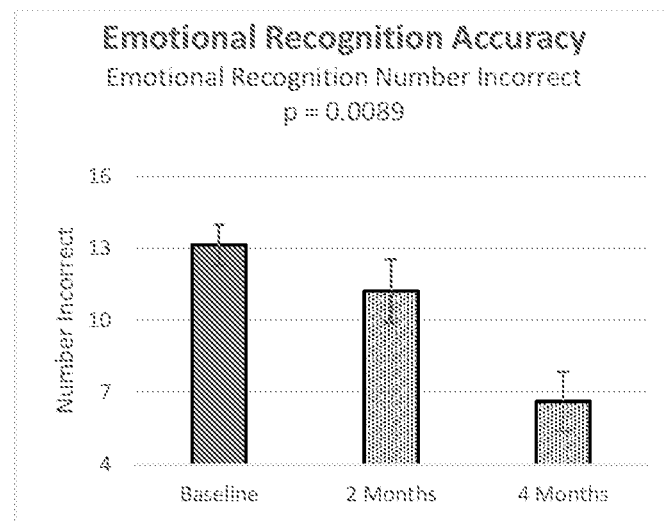
FIG. 17 shows results of emotional recognition accuracy tests (emotional recognition number incorrect) on human subjects during clinical trials at baseline and following 2 and 4 months dosing with compositions of the instant invention.
Figure 18:
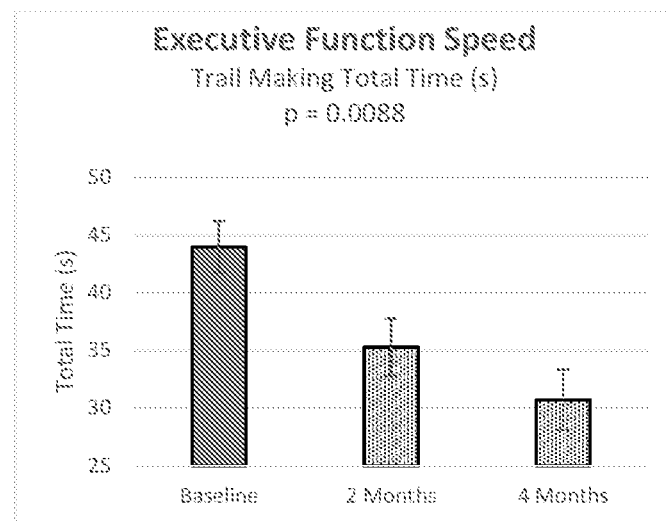
FIG. 18 shows results of executive function speed tests (trail making total times) on human subjects during clinical trials at baseline and following 2 and 4 months dosing with compositions of the instant invention.
Figure 19:
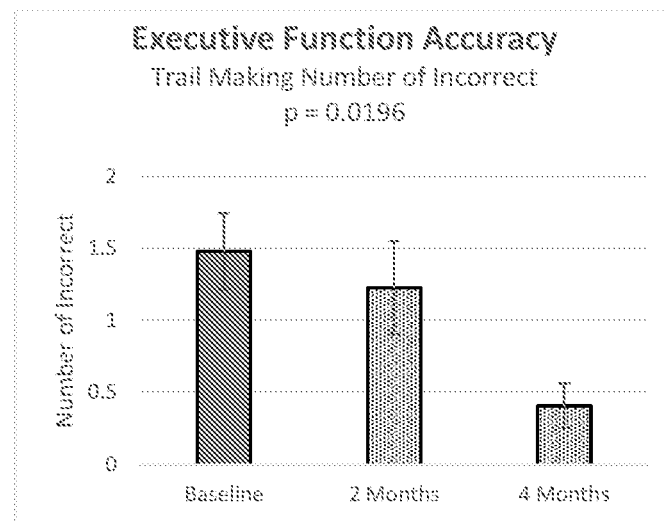
FIG. 19 shows results of executive function accuracy tests (trail making number of incorrect) on human subjects during clinical trials at baseline and following 2 and 4 months dosing with compositions of the instant invention.
Figure 20:
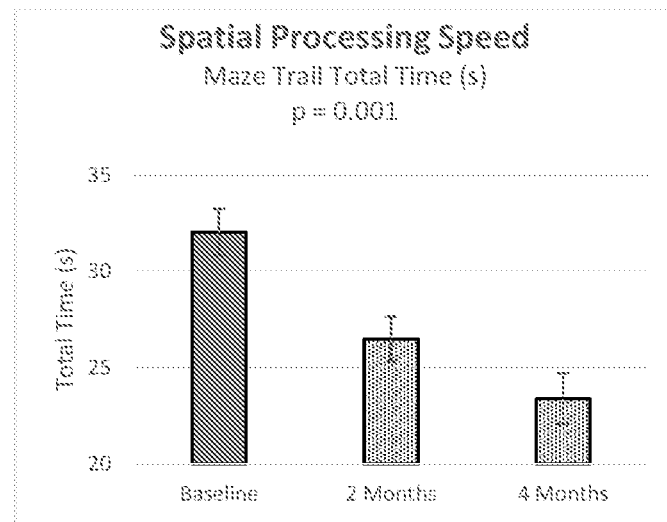
FIG. 20 shows results of spatial processing speed tests (maze trail total times) on human subjects during clinical trials at baseline and following 2 and 4 months dosing with compositions of the instant invention.
Figure 21:
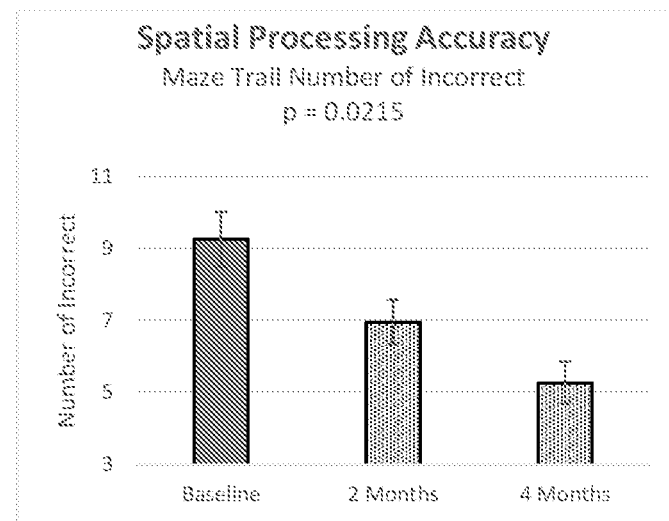
FIG. 21 shows results of spatial processing accuracy tests (maze trail number incorrect) on human subjects during clinical trials at baseline and following 2 and 4 months dosing with compositions of the instant invention.
Figure 22:
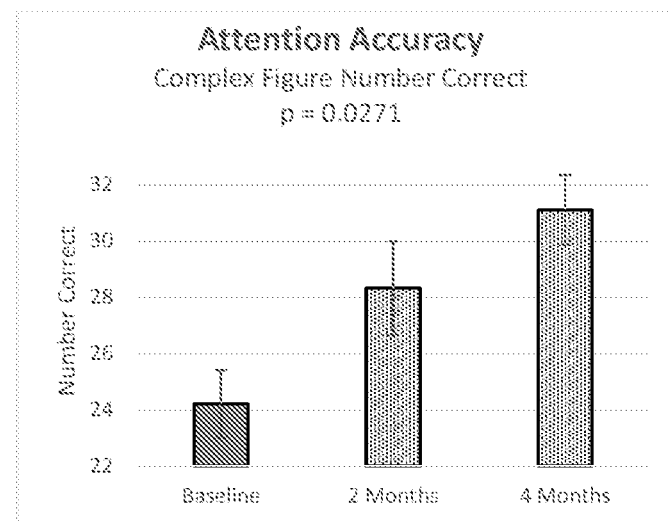
FIG. 22 shows results of attention accuracy tests (complex figure number correct) on human subjects during clinical trials at baseline and following 2 and 4 months dosing with compositions of the instant invention.
Figure 23:
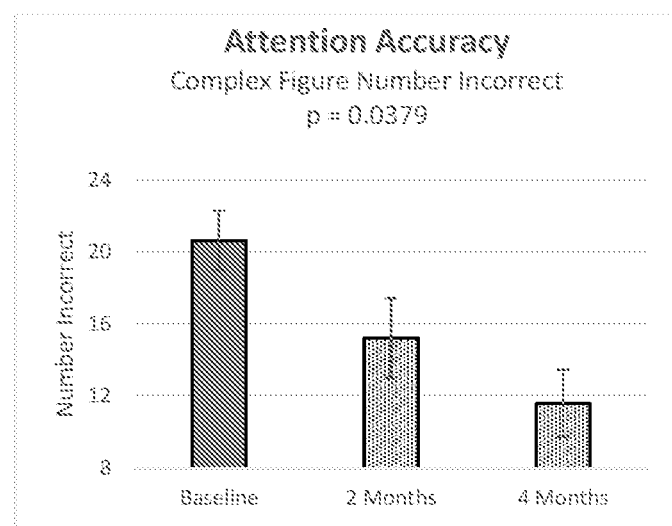
FIG. 23 shows results of attention accuracy tests (complex figure number incorrect) on human subjects during clinical trials at baseline and following 2 and 4 months dosing with compositions of the instant invention.

Two formulations (formulation 1 and formulation 2) were tested to assess their effects on various aspects of human cognition. These tests are well known to those skilled in the art and described generally in references 72-104, which are all incorporated herein by reference. Healthy adults between the ages of 30 and 80 were administered a plurality of tests every 8 weeks to measure cognitive health and mental performance. Formulation 1 was administered to 15 participants with an average age of 44. Formulation 2 was administered to 26 participants with an average age of 62. The results of tests of formulation 1 is presented in FIGS. 1-9. The results of tests of formulation 2 are presented in FIGS. 10-23.

Formulation 1:

A) Vitamin E (d-alpha-tocopherol succinate (1,210 IU/g)) Concentration/Pill: 83 mg (100 IU); B) Alpha-Lipoic Acid (99%) Concentration/Pill: 50 mg; C) *Centella asiatica* Extract—Whole Plant, Concentration/Pill: 200 mg—(20% Asiaticosides ~40 mg); D) *Panax Ginseng* Extract—Root Extract Concentration/Pill: 175 mg—(Std. to 5% Ginsenosides ~8.75 mg); E) Selenium (L-Selenomethionine) 0.5% Se, Concentration/Pill: 25 mcg. Suggested dosage: 2 pills/capsules per day, preferably with food taken together in the morning. Pills/capsules may comprise other constituents as would be understood by a person of skill in the art, for example, but not limited to microcrystalline cellulose, magnesium stearate, silicon dioxide and the like.

Formulation 2:

A) Vitamin E (d-alpha-tocopherol succinate (1,210 IU/g)) Concentration/Pill: 125 mg (150 IU); B) Alpha-Lipoic Acid (99%) Concentration/Pill: 100 mg; C) *Centella asiatica* Extract—Whole Plant, Concentration/Pill: 175 mg—(20% Asiaticosides ~35 mg); D) *Panax Ginseng* Extract—Stems & Leaves Concentration/Pill: 150 mg—(Std. to 5% Ginsenosides ~7.5 mg); E) Selenium (L-Selenomethionine) 0.5%

Se, Concentration/Pill: 25 mcg. Suggested dosage: 2 pills/capsules per day, preferably with food, taken together in the morning.

The results of the tests presented in FIGS. 1-23 suggest that the compositions/formulations as described herein can be used to enhance and/or increase spatial processing and memory, working memory, executive function, multi-tasking, verbal learning, emotional recognition, visuospatial processing or any combination thereof in subjects. Further, the results of the tests presented in FIGS. 1-23 suggest that the compositions/formulations as described herein can be used to prevent decline in spatial processing and memory, working memory, executive function, multi-tasking, verbal learning, emotional recognition, visuospatial processing or any combination thereof in subjects.

In addition to the results presented in the figures and as described above, subjects administered the formulations noted perceived increases in or more of: short and long-term memory, increased ability to learn new tasks, better quality sleep, higher energy levels, enhanced mood, enhanced ability to focus, decreased stress levels, increased confidence, better drive, less migraines, and reduced cognitive impairment from lack of sleep.

The specific formulations and compositions described herein also exhibit novel features and characteristics in terms of the individual components in the composition, their amounts, process by which they are obtained and their dosage recommendation. For example, but not to be considered limiting in any manner, *Ginseng* root extract is preferred over *Ginseng* stem and leaf extract for the reduction of adverse effects, such as, but not limited to indigestion in subjects. Similarly, formulations comprising high concentrations of asiaticosides, for example 40% asiaticoside concentration was associated with the adverse effect of lucid dreams within subjects. Formulations comprising 20% w/w asiaticoside concentrations (or less) is associated with a significantly decreased risk of such an adverse effect. Also, formulations taken on an empty stomach result in greater instances of acid reflux and/or indigestion in subject populations. Thus, it is preferable that the formulations be taken with food. Additionally, when taken at night, the formulations can cause wakefulness and an inability to sleep. Thus, it is preferable that the formulations be taken in the morning only.

What is claimed is:

1. A composition in a unit dose form comprising:
   *Centella asiatica* extract, the extract comprising 20-80 mg of asiaticosides;
   d-α-tocopherol succinate in an amount of 40-200 mg;
   *Ginseng* root extract, the extract comprising 4-20 mg of ginsenosides;
   L-selenomethionine in an amount of 10-50 mcg, and;
   α-lipoic acid in an amount of 25-200 mg;
   wherein the asiaticosides are present in an amount of 20% w/w or less of the composition and the ginsenosides are present in an amount of 5% w/w or less of the composition.

2. The composition of claim 1 comprising about 50 mg or 100 mg of lipoic acid, about 25 mcg of L-selenomethionine, about 83 mg or 125 mg of d-α-tocopherol succinate, about 200 mg or 175 mg of *Centella asiatica* whole plant extract providing about 40 mg or 35 mg of asiaticosides, respectively; and 175 mg or 150 mg of *Panax Ginseng* extract comprising about 8.75 mg and 7.5 mg of ginsenosides, respectively.

3. The composition of claim 1 further comprising one or more pharmaceutically acceptable excipients.

4. The composition of claim 3 wherein the one or more pharmaceutically acceptable excipients are selected from the group consisting of microcrystalline cellulose, magnesium stearate, silicon dioxide and combinations thereof.

5. A method for treating symptoms of cognitive decline in a subject in need thereof by administering the composition of claim 1 to the subject.

6. The method of claim 5, wherein the cognitive decline is normal age-related cognitive decline.

7. The method of claim 5, wherein the cognitive decline is a loss of cognitive function, loss of memory, memory impairment, loss of short term memory, loss of intermediate term memory, loss of long term memory or loss of an ability to learn, store or recall information, loss of attention span, loss of language skills, loss of writing skills or loss of problem solving skills.

8. The method of claim 7, wherein the cognitive decline is from a degenerative disease or disorder.

9. The method of claim 8, wherein the degenerative disease or disorder is Alzheimer's disease, Lewy body dementia, vascular dementia, Parkinson's disease-associated dementia, Huntington's disease-associated dementia, AIDS-associated dementia, benign senile forgetfulness, Down's syndrome-associated dementia, multi-infarct dementia, multiple sclerosis, tardive dyskinesia, Wernicke-Korsakoff syndrome or alcoholism-associated dementia.

10. A method of making the composition of claim 1 comprising,
    combining d-alpha-tocopherol succinate, alpha-lipoic acid, *Centella asiatica* extract, *Panax ginseng* root extract and L-selenomethionine, wherein *Centella asiatica* extract and *Panax ginseng* root extract are derived from water-ethanol extractions.

11. The method of claim 10, further comprising packaging the composition in a capsule with microcrystalline cellulose, magnesium stearate and silicon dioxide.

* * * * *